United States Patent [19]

Schemmel et al.

[11] Patent Number: 5,272,442
[45] Date of Patent: Dec. 21, 1993

[54] ELECTRICAL FEED-THROUGH BUSHING CAVITY INSULATION DETECTOR

[75] Inventors: Dean J. Schemmel, New Berlin; Charles M. Martin; Augusto D. Hernandez, both of Waukesha, all of Wis.

[73] Assignee: Cooper Power Systems, Inc., Corapolis, Pa.

[21] Appl. No.: 913,002

[22] Filed: Jul. 14, 1992

Related U.S. Application Data

[63] Continuation-in-part of Ser. No. 670,941, Mar. 18, 1991, Pat. No. 5,140,270.

[51] Int. Cl.$^5$ ............................................. G01R 31/12
[52] U.S. Cl. .................................. 324/552; 324/553; 324/674
[58] Field of Search ................ 324/551, 552, 553, 663, 324/674

[56] References Cited

U.S. PATENT DOCUMENTS

| | | | |
|---|---|---|---|
| 2,130,865 | 5/1936 | Watts et al. | 324/552 |
| 2,333,532 | 2/1941 | Frakes et al. | 324/552 |
| 2,472,814 | 7/1945 | Elliott | 324/551 |
| 4,833,415 | 5/1989 | Nourai et al. | 324/557 |
| 5,140,270 | 8/1992 | Martin et al. | 324/552 |

Primary Examiner—Kenneth A. Wieder
Assistant Examiner—Glenn W. Brown
Attorney, Agent, or Firm—Wigman, Cohen, Leitner & Myers

[57] ABSTRACT

Apparatus for detecting the sufficiency and quality of an amount of dielectric material contained in the cavity of a transformer bushing is disclosed. The apparatus comprises a collar assembly which when placed over the bushing forms a capacitive element, a tunable signal producer for applying a signal to the capacitive element, a circuit for receiving, amplifying and rectifying the output signal from the capacitive element, and an indicator to detect and indicate the dielectric condition or capacitance of the capacitive element and thus the sufficiency and/or quality of the dielectric material within said bushing assembly. The collar assembly in one embodiment comprises a pair of electrically conductive segments which are hinged together for positioning about the bushing. The interior surfaces of the collar assembly are shaped to conform substantially to the outer shape of the transformer bushing.

18 Claims, 4 Drawing Sheets

ELECTRICAL FEED-THROUGH BUSHING CAVITY INSULATION DETECTOR

CROSS-REFERENCE TO RELATED APPLICATION

This is a continuation-in-part of U.S. patent application Ser. No. 07/670,941 filed Mar. 18, 1991, now U.S. Pat. No. 5,140,270.

FIELD OF THE INVENTION

The present invention relates to the detection of faulty dielectric conditions which may exist internally in transformer feed-through insulators, known as bushings, usually used on distribution power transformers. The invention comprises a removable collar and associated electronic circuitry which will produce a measurable indication to the user of the absence of a dielectric filler which may exist in assembled bushings.

BACKGROUND OF THE INVENTION

In order to connect distribution transformers to utility power lines, it is necessary to provide an electrically conductive path through the wall of a sealed and grounded case to an inside assembly. Such connections are typically accomplished by means of a device known as a feed-through bushing. Feed-through bushings are constructed of two types of materials, namely, an electrical conductor and an electrical insulator. A typical bushing comprises an inner electrical conductor of copper or other electrically conductive material surrounded by an electrical insulator of porcelain or an equivalent insulating material. If a bushing is designed to withstand high voltage applications, (14,000 VAC and higher), it may be necessary to provide the bushing with an inner cavity surrounding the conductor and to fill the cavity with an additional insulator of high dielectric strength, such as transformer oil. In the event this additional dielectric filler is omitted or has partially leaked from the bushing, an electrical failure of the bushing in high voltage applications may occur.

Another problem may exist with this arrangement which can cause the generation of radiated noise in the form of radio frequencies. This radiation is usually of sufficient magnitude as to interfere with radio frequency reception (TV, radio, etc.). Such radiation is produced in the bushing due to partial discharges between the bushing conductor and ground, typically caused by insufficient or faulty insulation. A bushing operating under this condition may eventually fail electrically. The present invention detects the condition causing the two above-described problems.

SUMMARY OF THE INVENTION

The present invention comprises a removable collar for the bushing and associated electronic circuitry which will discriminate between acceptable and marginal or defective electrical high voltage bushings.

In one embodiment of the invention, the removable collar is fabricated from a conductor and an insulator and is assembled in a tubular laminated construction of cylindrical or conical shape. In another embodiment of the invention, which is a presently preferred embodiment, the removable collar is cast or machined in two parts from an electrically conductive material, such as aluminum, so as to form-fit the particular bushing to be tested. The two collar parts are preferably hinged together in a "clam shell" arrangement to permit rapid installation and removal of the collar. The form-fitting configuration minimizes the volume of air space between the collar and bushing exterior. Air has a lower dielectric constant than both insulator material and its associated dielectric medium. The effect of this air is two fold. It lowers the capacitance of the detecting circuit and it lowers the difference in capacitance between the two conditions being detected. The result is the tuned detecting circuit must be operated at a relatively high frequency and the circuit is less discriminating between an empty bushing and a filled bushing. This embodiment eliminates the problems mentioned above and has additional advantages which will become clear as explained later.

When the collar of either embodiment is placed over or about the outer insulating surface of a bushing, the conductor of the collar functions as one element of a capacitor. The total capacitance of the collar and bushing combination is determined by the following elements: (1) the bushing inner conductor; (2) the dielectric medium of the inner cavity; (3) the dielectric material of the outer shell of the bushing; and (4) the conductor of the removable collar. The element of this capacitive combination that is most likely to vary the greatest within a sampling of bushings of a given design is the insulating filler in the inner cavity volume. The cavity is usually filled with oil of transformer quality, and the volume and dielectric strength may not always be constant. For example, the oil may leak out or become contaminated by reason of defective seals.

By utilizing the capacitance formed by the collar, it is possible to detect variations in the dielectric strength of the filler in the inner cavity volume of the bushing. The present invention utilizes the capacitance in the following manner. A signal waveform, e.g., a 1 KHz to 50 KHz sinusoidal waveform, from a signal generator source is fed to a frequency discrimination circuit which is designed so that the collar and bushing capacitive combination form part of a frequency selective filter circuit. The signal that is passed through this circuit is amplified, rectified, again amplified and then presented as an output signal or indication. Because of the characteristics of this filter circuit, a slight change in capacitance, as detected from the collar and bushing combination, is presented as an output signal with considerable magnitude of change.

An effective method of using the device of this invention is to position the collar on a known acceptable bushing assembly, and calibrate the output as a comparison standard. The collar may then be positioned on a bushing of the same construction to be tested and another output reading is obtained. Any significant difference in the dielectric strength of the inner cavity volume of the tested bushing from that of the acceptable bushing will be apparent from a comparison of the outputs.

One of the advantages of the present invention is its simplicity and versatility of operation. The invention does not involve the use or measurement of a high voltage or current that may be hazardous to the operator. Moreover, it is not complex to set up and operate and can be used in both manufacturing and customer locations as a portable bushing testing device.

A present method employed for detecting faulty bushings is known as RIV (radio interference voltage) testing. This test procedure involves a complex set-up using a specially designed chamber, which must be shielded from all external random radio frequency signals. Special high voltage measuring devices must also be used.

DETAILED DESCRIPTION OF THE INVENTION

Figure 1:
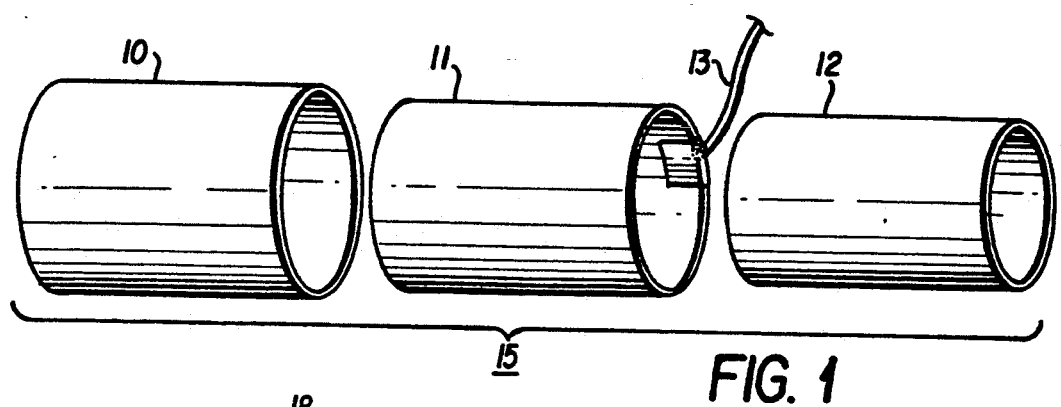
FIG. 1 is an exploded perspective view of one embodiment of a collar according to the present invention.

Referring to the exploded view of FIG. 1, a tubular collar 15 is formed of an assembly of three tubular components, an outer liner 10, an inner liner 12 and an intermediate tubular conductor 11 interposed between the inner liners. The outer and inner liners 10, 12 are constructed of an electrically insulating material and the intermediate conductive sleeve 11 is fabricated of an electrically conductive material, such as an electrically conductive metal foil, e.g., aluminum, copper or the like. If sleeve 11 has a sufficient wall thickness, outer and inner insulating liners 10, 12 may be eliminated if desired so that the test collar will comprise only the conductive sleeve 11. An electrical lead 13 is electrically connected to sleeve 11 by any suitable means, such as by soldering, welding or the like.

Figure 2:
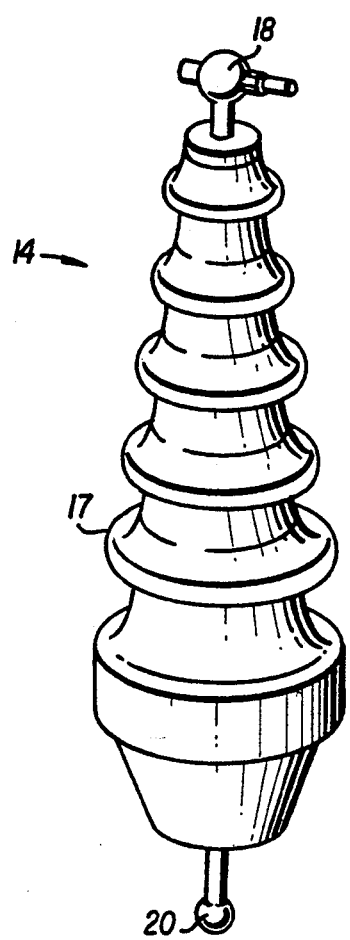
FIG. 2 is a perspective view of a transformer bushing assembly.

FIG. 2 illustrates a conventional transformer bushing 14 comprising a protective insulator or outer shell 17 with a conductive feed-through assembly passing through the longitudinal axis thereof. The feed-through assembly comprises a pair of terminals 18, 20 electrically connected to one another by a central conductor (not shown in FIG. 2) which extends through the protective insulator 17. The protective insulator 17 is typically made of porcelain or other material having a high dielectric strength.

Figure 3:
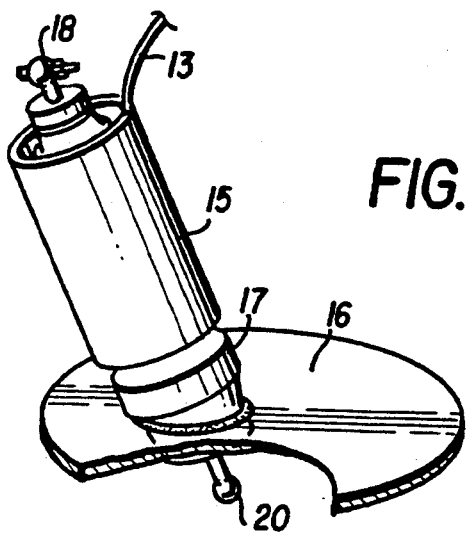
FIG. 3 is a perspective view of the collar of FIG. 1 installed over a bushing of the type shown in FIG. 2.

FIG. 3 illustrates a feed-through bushing of the type shown in FIG. 2 extending through the cover 16 of a pole-type transformer (not shown). The tubular collar 15 of FIG. 1 is installed over the protective insulator 17 of the bushing with the electrical lead 13 oriented upwardly. As will be appreciated by those skilled in the art, a capacitance exists between the tubular conductor 11 to which the lead 13 is connected and the feed-through conductor (not shown) to which the terminals 18, 20 are electrically connected.

Figure 4:
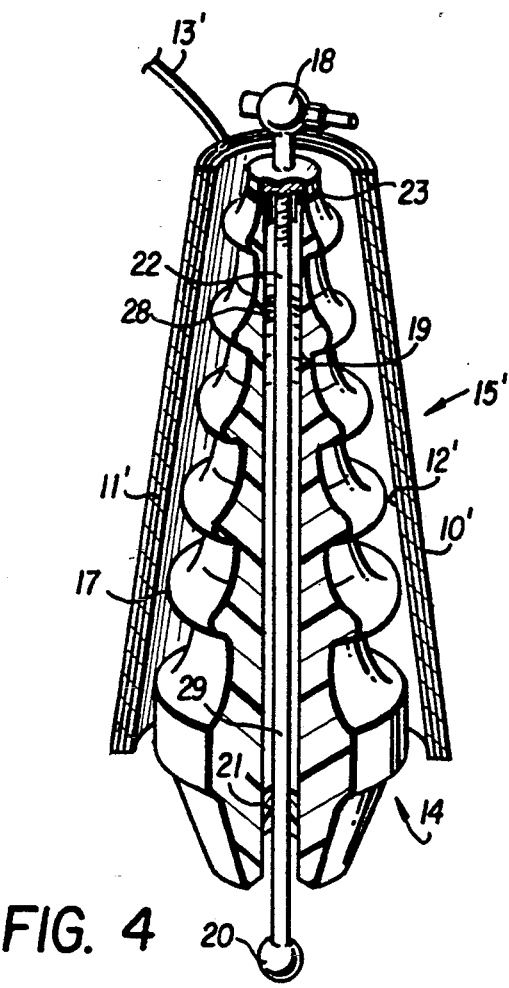
FIG. 4 is a perspective view, partly in section, of a collar of another design installed over a bushing.

Referring now to FIG. 4, there is shown another tubular embodiment of the collar of the invention designated generally by reference numeral 15'. Collar 15' is in the form of a hollow truncated cone and comprises outer and inner liners 10', 12' and an intermediate conductive sleeve 11' to which electrical lead 13' is electrically connected. The conical collar 15' is disposed about the bushing 14 which has an insulating outer shell 17 that also has a generally conical shape. The insulating shell has an elongated central cavity 22 which is filled with a dielectric filler, such as transformer oil 19, or any other suitable dielectric material. The bushing has a central conductor rod 29 that extends through the cavity 22 along the axis thereof. Rod 29 terminates at its lower end in terminal 20 and at its upper end in a threaded connection with terminal 18. The transformer oil 19 is sealed in the cavity 22 at the lower end of the bushing by a resilient stopper 21 through which rod 29 sealingly passes and at the upper end of the bushing by a gasket 23 which seals the upper end of the bushing cavity when the terminal 18 is threaded onto the upper end of the conductive rod 29.

The collar 15' forms a capacitor with the bushing 14 in the following manner: The center conductive rod 29 functions as the inner plate surface of the capacitor, the conductive sleeve 11' of the collar 15' functions as the outer plate surface of the capacitor, and the dielectric filler 19 and insulating outer shell 17 comprise the dielectric material of the capacitor. The magnitude of the capacitance of the FIG. 4 arrangement is influenced primarily by the type of dielectric filler 19 in the cavity 22 and the level 28 to which the cavity is filled. In the embodiments described herein, the dielectric filler 19 is a transformer oil retained in the cavity by the stopper 21 and gasket seal 23. A small air space is provided above the filler level 28 to allow for expansion of the transformer oil due to the thermal conditions to which the bushing may be subjected.

Figure 7:
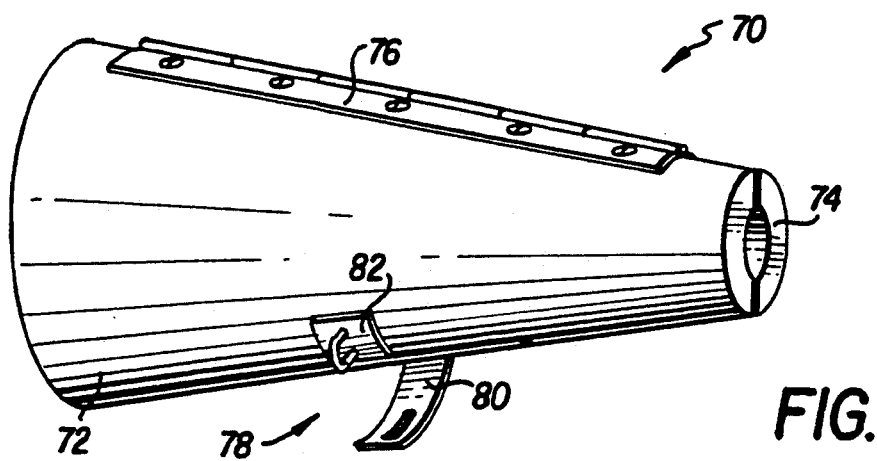
FIG. 7 is a perspective view of a presently preferred embodiment of a removable collar according to the present invention.
Figure 8:
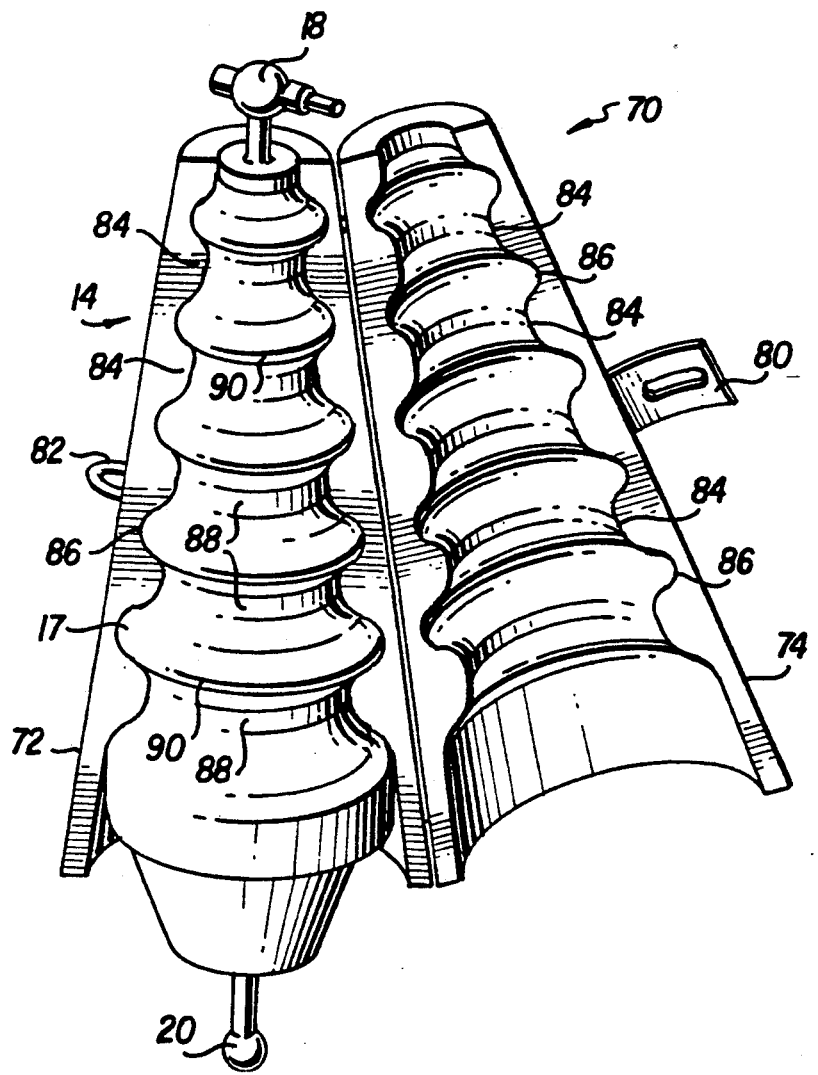
FIG. 8 is a perspective view of the removable collar of FIG. 7 shown ready for installation about a bushing.

FIGS. 7 and 8 illustrate a presently preferred embodiment of the removable collar of the invention which is designated generally by reference numeral 70. Collar 70 comprises a hollow truncated conical element made in two identical parts, a first truncated conical segment 72 and a second truncated conical segment 74. The segments 72, 74 are made of an electrically conductive material, preferably a conductive metal, such as copper, aluminum or alloys thereof.

While the collar 70 is illustrated and described herein as a truncated conical element, it is contemplated within the scope of the invention that the collar 70 have any suitable external shape and cross-section, including a cylindrical shape as well as round or polygonal cross-sections. What is important is that the internal circumferential surface of the collar 70 be form-fitted to the exterior shape of the transformer bushing 14. That is, the interior surfaces of the collar segments 72, 74 should conform substantially to the outer shaped surfaces of the bushing. It should also be understood that there are a number of sizes and forms of transformer bushings and that the collar 70 may be constructed to form-fit a particular size and design of the transformer bushing so as to minimize the air space between the interior surface of the collar 70 and the exterior surface of the bushing 14.

Referring again to FIG. 7, the two equivalent segments 72, 74 of the collar 70 are hingedly joined together along adjacent edges by an elongated hinge member 76 so as to be hingedly connected together in "clam shell" fashion. Any suitable form of hinge may be used. Means 78 are also provided for securing the two segments 72, 74 in the closed position shown in FIG. 7. In the embodiment shown, means 78 comprises a hasp 80 and staple 82 although any other suitable closure fastener may be used, such as a quick-release toggle fastener or the like.

Referring now to FIG. 8, the collar 70 is shown with conical segment 72 positioned around the bushing 14 and the conical segment 74 hinged away from segment 72. The interior surface of each segment is provided with a plurality of semicircular ridges 84 and grooves 86 configured to form-fittingly mate with corresponding annular grooves 88 and rings 90 of the bushing 14.

When the conical segment 74 is hinged to the closed position about bushing 14 and the means 78 (80, 82) are secured together, the air space between the confronting exterior and interior surfaces of the bushing 14 and collar 70, respectively, are minimized. The collar 70 may be manufactured by machining or, preferably, by casting a conductive metal, such as aluminum, about a form.

Figure 5:
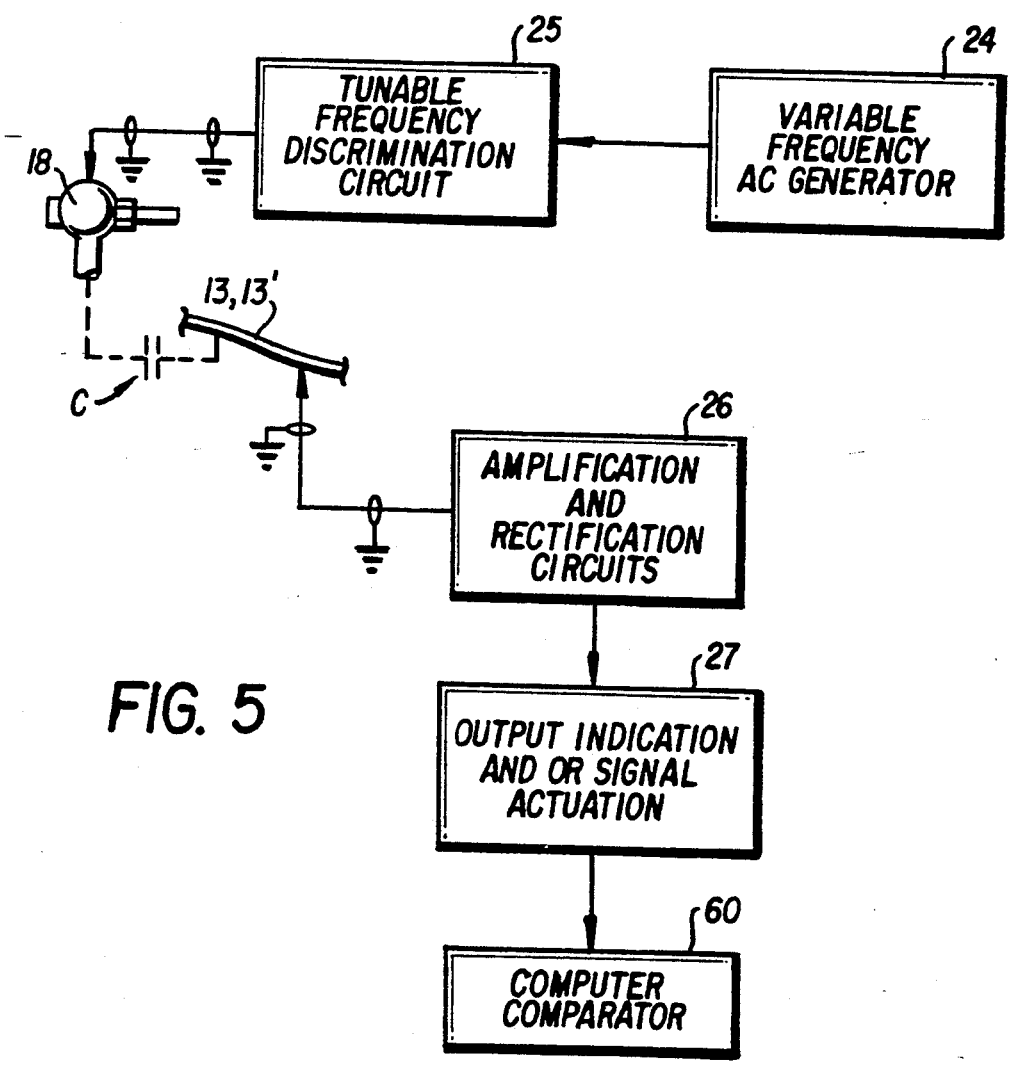
FIG. 5 is a block diagram the dielectric testing device of the invention showing the electrical connections to the collar and bushing.

Referring now to FIG. 5, there is shown a testing circuit suitable for use with the collars of the invention in block diagram form. Connection of this circuit to one of the bushing terminals 18, 20 and to the electrical lead 13, 13' places the capacitive arrangement of FIGS. 3-4 or 7-8 into the circuit as the capacitor C shown in dotted lines in FIG. 5.

The testing circuit of FIG. 5 operates in the following manner: A sinusoidal signal from a signal generator 24, such as a TEKTRONIX FG #501A, is coupled to a tunable frequency selective circuit 25, which is, in turn, connected to terminal 18 of the bushing capacitor plate of capacitor C. By capacitive coupling through the dielectric filler 19 and insulator shell 17, the applied signal is coupled to the conductive sleeve 11' (or 11 or 70) which comprises the collar capacitor plate of capacitor C. The signal is then fed by electrical lead 13' (or 13) to the input of amplification and rectification circuits 26 where the signal is amplified and rectified to a DC output which is connected to an output indicating/signal actuation device 27. Device 27 may be, for example, a meter, such as a digital Beckman MOD #4410, oscilloscope, indicator lamps or the like. The output signal is directly proportional to the signal detected by the capacitor C and is, therefore, a direct indication of the dielectric condition of the bushing 14.

If desired, a computer comparator 60 may be connected to the output indicator 27 or to the output of amplification and rectification circuits 26. The computer 60 contains previously stored values of the output signals for an acceptable range of dielectric conditions, e.g., the dielectric conditions for a predetermined type and level of dielectric filler in the bushing cavity. Upon request, the computer 60 can determine for a given bushing and dielectric filler the amount of filler contained in the cavity. The manner of programming a computer to achieve the above result will be apparent to those skilled in the art.

Figure 6:
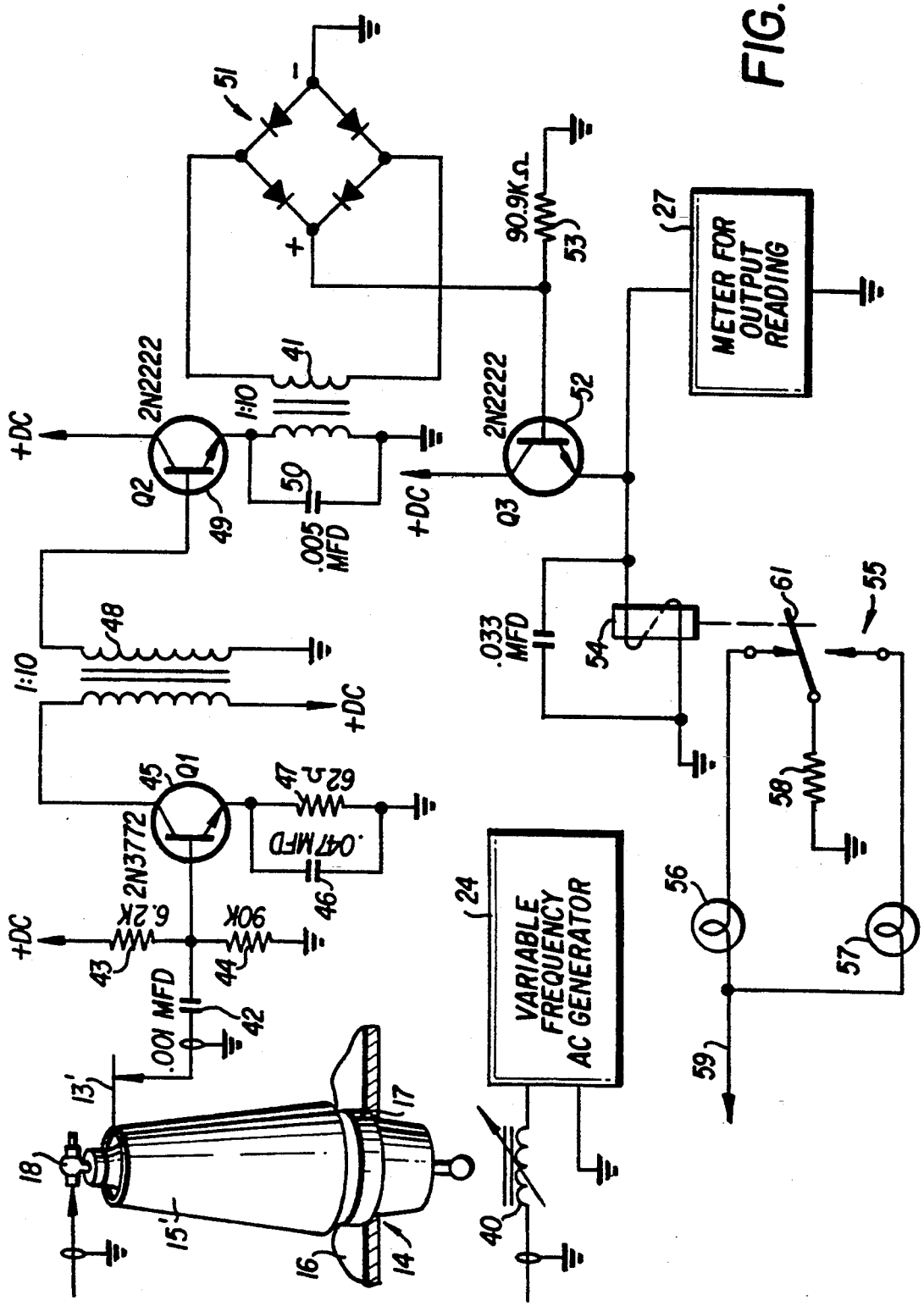
FIG. 6 is a circuit diagram of the dielectric testing device of the invention.

FIG. 6 illustrates in greater detail one circuit that has been used to measure the dielectric condition of transformer feed-through bushings using the collar 15'.

A sinusoidal signal of relatively low voltage (0.1 VAC to 0.5 VAC) is produced by generator 24 and fed to a frequency selective filter circuit which comprises a tunable inductor coil 40 connected in series with the capacitor of the bushing 14 and collar 15' combination, i.e., capacitor C in FIG. 5. A series-type filter circuit as used in this arrangement will pass only a limited band of frequencies and will reject all other frequencies. The frequency band that this circuit will pass is dependent upon the values of the tunable inductor 40 (in henrys) and the collar-to-bushing capacitance (in farads). The circuit of FIG. 6 will also be operative to accomplish the desired objective if the tunable inductor 40 is connected to the output of the collar 15' at electrical lead 13'.

In a test using the test circuit shown, the tunable inductor center adjustment value was 24.5 millihenrys and the collar-to-bushing capacitance with transformer oil in the bushing cavity was 413 picofarads. This combination of inductance and capacitance produces a frequency selective circuit with a nominal center frequency value of approximately 50 KHz. By adjusting the signal generator 24 to 50 KHz at an amplitude level of 1.4 millivolts AC RMS, and by adjusting the ferrite core in the tunable inductor coil, a peak output signal is produced at the collar output lead 13'. This signal is then amplified by the electronic circuitry of amplifier stages Q-1 and Q-2 which comprise capacitor 42, resistors 43, 44, transistor 45, an RC network 46, 47, transformer 48, transistor 49, and capacitor 50. The amplified signal at the output of transformer 41 is rectified by a bridge rectifier 51 to a DC-type signal. Amplification stage Q-3 comprising transistor 52 and ground resistor 53 gives additional amplification to the DC signal. The signal at the output of stage Q-3 (emitter output of transistor 52) is of sufficient strength to operate a device such as a meter 27 or an oscilloscope for operator evaluation. The output signal from amplifier stage Q-3 may also be sensed by a DC relay 54 which may be coupled to a lamp indicator circuit 55 comprising a pair of lamps or LEDs 56, 57 and a current limiting resistor 58 supplied by a feed voltage at line 59. In the position of relay 54 and switch 61 shown in FIG. 6, lamp or LED 56 is lighted. When relay 54 operates upon sensing an output signal from Q-3 at or above a predetermined DC voltage, switch 61 shifts to light lamp or LED 57 and lamp or LED 56 is turned off.

In a test conducted on a 14,400 volt porcelain, oil-filled bushing, an applied signal of 50 KHz at a level of 0.14 volts RMS produced a reading of 10.7 volts DC on output meter 27 by adjustment of the tunable inductor 40. The same bushing with its cavity drained of the oil and measured without changing the initial circuit adjustments produced an output meter reading of 0.5 volts DC. It was also determined that intermediate levels of oil in the inside cavity, between empty and full, produced proportional changes in the output meter readings. The foregoing test demonstrates that the present invention is capable of determining the quantity of oil, or other dielectric filler in the inside sealed cavity of an electrical bushing.

It has been found that use of the collar 70 shown in FIGS. 7 and 8 not only results in greater accuracy by reason of the elimination of air spaces between the collar and bushing, but also permits the test to be performed at even lower frequencies than the 50 KHz used for the circuit shown in FIG. 6. Frequencies as low as 1-2 KHz may be used in a circuit similar to that of FIG. 6 with an appropriate selection of components that is well within the capability of one skilled in the art. A significant advantage of using a lower frequency is the minimization of signal radiation and stray pick-up problems.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. Apparatus for testing the dielectric conditions of a bushing having an insulative shell with a cavity therein for containing a dielectric filler and a conductive member extending through said cavity, comprising:

collar means comprising a conductive sleeve formed in two segments and being adapted to surround the insulative shell of said bushing for forming a capacitor with said conductive member;

first circuit means connected to one of said conductive member and conductive sleeve for applying a low voltage input signal thereto; and second circuit means connected to the other of said conductive member and conductive sleeve for receiving an output signal therefrom, said output signal being indicative of the dielectric condition of the dielectric filler contained in the cavity of said bushing.

2. The apparatus of claim 1, including means for hingingly connecting said two segments together and means for releasably holding said two segments together in surrounding relation to the insulative shell of said bushing.

3. The apparatus of claim 1, wherein the insulative shell of the bushing has an outer shaped surface, said two segments having interior surfaces shaped to conform substantially to the outer shaped surface of the insulative shell whereby the space between the outer shaped surface of the insulative shell and the interior surfaces of said two segments is minimized.

4. The apparatus of claim 3, wherein the conductive sleeve is an electrical conductor.

5. The apparatus of claim 3, wherein said conductive sleeve is made of an electrically conductive metal.

6. The apparatus of claim 3, wherein said conductive sleeve is cast aluminum.

7. The apparatus of claim 1 wherein said collar means is in the form of a hollow truncated cone.

8. The apparatus of claim 1, wherein said collar means is in the form of a cylindrical sleeve.

9. The apparatus of claim 1, wherein the magnitude of the output signal is indicative of the quantity of dielectric filler in the bushing cavity.

10. The apparatus of claim 1, wherein said dielectric filler is transformer oil.

11. A collar for use in an apparatus for testing the dielectric conditions of a bushing having an insulative shell with a cavity and an outer shaped surface and including a conductive member extending through said cavity, said collar comprising a conductive sleeve adapted to surround the insulative shell of said bushing for forming a capacitor with said conductive member, said sleeve comprising two segments having interior surfaces shaped to conform substantially to the outer shaped surface of the insulative shell.

12. The collar of claim 11, wherein said segments form a hollow truncated cone.

13. The collar of claim 11, including hinge means for releasably holding said two segments together in surrounding relation to the insulative shell of said bushing.

14. The collar of claim 11, wherein said conductive sleeve is made of an electrically conductive material.

15. The collar of claim 14, wherein the electrically conductive material is metal.

16. The collar of claim 11, wherein said conductive sleeve is cylindrical.

17. The collar of claim 11, wherein the interior surfaces of said segments are formed with annular ridges and grooves.

18. The method of testing a dielectric-filled bushing comprising:

generating a low voltage test signal;

coupling said test signal via a capacitor formed by said bushing and a conductive sleeve surrounding said bushing through a frequency-selective filter; and sensing the test signal output from said filter and relating the output to a dielectric quantity.

* * * * *